(12) United States Patent
Bakker et al.

(10) Patent No.: US 9,291,558 B2
(45) Date of Patent: Mar. 22, 2016

(54) LUMINESCENCE BASED SENSOR

(75) Inventors: Jim Writser Peter Bakker, Uppsala (SE); Ove Ohman, Uppsala (SE); Dirk Kurzbuch, Dublin (IE); Thomas Ruckstuhl, Zurich (CH); Brian MacCraith, Dublin (IE); Stephen O'Driscoll, Dublin (IE)

(73) Assignees: Dublin City University, Dublin (IE); Amic AB, Uppsala (SE)

( * ) Notice: Subject to any disclaimer, the term of this patent is extended or adjusted under 35 U.S.C. 154(b) by 335 days.

(21) Appl. No.: 13/697,278

(22) PCT Filed: May 11, 2011

(86) PCT No.: PCT/EP2011/057653
§ 371 (c)(1),
(2), (4) Date: May 20, 2013

(87) PCT Pub. No.: WO2011/141530
PCT Pub. Date: Nov. 17, 2011

(65) Prior Publication Data
US 2013/0236982 A1    Sep. 12, 2013

(30) Foreign Application Priority Data

May 12, 2010 (GB) .................................. 1007921.8

(51) Int. Cl.
| | |
|---|---|
| *G01N 21/76* | (2006.01) |
| *G01N 21/64* | (2006.01) |
| *G01N 33/543* | (2006.01) |
| *G01N 21/66* | (2006.01) |

(52) U.S. Cl.
CPC .............. *G01N 21/64* (2013.01); *G01N 21/645* (2013.01); *G01N 21/648* (2013.01); *G01N 21/6452* (2013.01); *G01N 21/66* (2013.01); *G01N 21/76* (2013.01); *G01N 33/54373* (2013.01)

(58) Field of Classification Search
None
See application file for complete search history.

(56) References Cited

U.S. PATENT DOCUMENTS

| | | |
|---|---|---|
| 2007/0262265 A1 | 11/2007 | MacCraith et al. |
| 2009/0163377 A1 | 6/2009 | Alexandre et al. |

FOREIGN PATENT DOCUMENTS

| | | |
|---|---|---|
| JP | 2008-298771 A | 12/2008 |
| WO | 02/059583 A1 | 8/2002 |
| WO | 2009/021964 A2 | 2/2009 |

OTHER PUBLICATIONS

Krieg, A. et al. Towards single-molecule DNA sequencing: Assays with low nonspecific adsorption, 2006, Analytical Biochemistry, vol. 349, pp. 181-185.*

(Continued)

*Primary Examiner* — Robert Xu
(74) *Attorney, Agent, or Firm* — Seed IP Law Group PLLC (57) ABSTRACT

A sensor comprising a substrate (100) having a first surface (105) and a second surface (110) is described. The first surface has at least one sensor site (115) provided thereon. The substrate is configured such that on excitation of a sample provided at the sensor site, luminescence originating from the sensor site propagates into the substrate, the second surface of the substrate being configured to selectively transmit the luminescence propagating within the substrates at angles greater than the critical angle out of the substrate where it may be detected by a detector (160) provided below the substrate.

20 Claims, 7 Drawing Sheets

(56) References Cited

OTHER PUBLICATIONS

Kurzbuch et al., "A Biochip Reader Using Super Critical Angle Fluorescence," Sensors and Actuators B 137:1-6, 2009.

International Search Report, mailed Dec. 1, 2011, for PCT/EP2011/057653, 5 pages.

\* cited by examiner

LUMINESCENCE BASED SENSOR

CROSS-REFERENCE TO RELATED APPLICATION

This application is a U.S. national stage application filed under 35 U.S.C. §371 of International Patent Application PCT/EP2011/057653, accorded an international filing date of May 11, 2011, which is incorporated herein by reference in its entirety.

FIELD

The present application relates to sensor and in particular to sensors based on collection of generated luminescence. The invention more particularly relates to sensor which operably collects light initially propagating within a substrate at angles greater than the critical angle—so called super critical angle luminescence to provide information on one or more target analytes.

BACKGROUND

Planar substrates, made from either glass (e.g. microscope slide) or optical polymer (e.g. Zeonex), are widely used in fluorescence-based optical chemical and biological sensors as a low-cost surface onto which multiple sensor or biorecognition sites can be patterned. Following excitation, the fluorescence from these sensor sites can be detected by placing a CCD- or CMOS-based imaging system below the substrate. However, this configuration results in low fluorescence collection efficiency due to a combination of the anisotropic nature of the fluorescence emission and the light-guiding behaviour of the substrate which results in a significant proportion of the emitted fluorescence being trapped within the substrate by total internal reflection (TIR). In addition, for many such configurations, the numerical aperture (NA) of the detection optics is low resulting in only a small fraction of the transmitted fluorescence being received by the detector. Given that this imposes a significant limitation on the optical detection performance of this sensor type, a number of strategies have been proposed to improve their optical detection sensitivity. However, a common feature of these strategies is a trade-off between the usability of the substrate for patterning and the enhancement in fluorescence collection efficiency achieved. For example, one such strategy involves the collection of a specific type of luminescence, fluorescence, and more specifically a type of fluorescence known as supercritical angle fluorescence (SAF) by integrating optical elements onto the top surface of the substrate. The SAF light typically propagates within the substrate at angles within the range of ~61.5-75°. These known optical elements however can affect the continuous nature of the sensor's top surface which is not optimal.

There is therefore a need for a luminescence based sensor configured for optimal configuration of super critical angle light without affecting the configuration of the top surface of the sensor.

SUMMARY

These and other problems are addressed by a sensor in accordance with the present teaching which incorporates an optical redirection element into a lower surface of the sensor substrate, the optical redirection element being configured to preferentially transmit light emitted from a sensor site on an upper surface of the substrate and propagating into the substrate at angles greater than the critical angle out of the substrate. The light transmitted out of the substrate may then be redirected by use of a complimentary optical element which is arranged relative to the substrate to provide for a redirection of the light transmitted by the substrate towards a detector. The detector is optimally located below the substrate. Such a sensor facilitates collection of supercritical angle light, and by preserving the continuous nature of the substrate's upper surface, allows the benefits of supercritical angle light collection to be brought to optical sensor applications that require the patterning of sensor sites on that upper surface. The preferential transmission of the supercritical angle light may in certain arrangement provide a redirection of the supercritical angle light through a refraction process, the optical redirection element providing a refractive optical element. It will be understood that within the present specification the term supercritical angle light refers to that light which would typically propagate within a substrate at angles greater than the critical angle and as such would be totally internally reflected at an inner surface of the substrate. In accordance with the present teaching such light is redirected out of the substrate where it may be subsequently detected using a detector.

Accordingly, a first embodiment of the application provides a sensor as detailed in claim 1. The application also provides a method as detailed in claim 25. Advantageous embodiments are provided in the dependent claims.

BRIEF DESCRIPTION OF THE DRAWINGS

The present application will now be described with reference to the accompanying drawings in which.

DETAILED DESCRIPTION OF THE DRAWINGS

Figure 1:
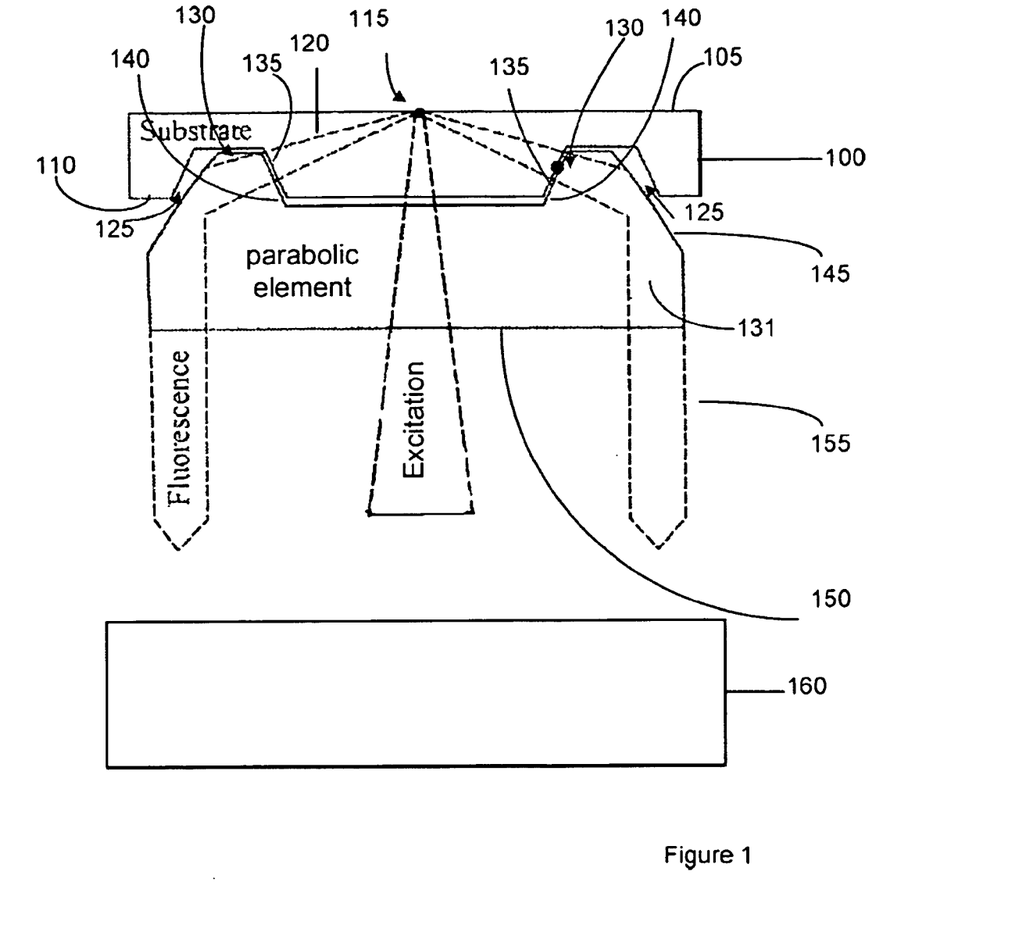
FIG. 1 is a schematic showing a first embodiment of components of a sensor system in accordance with the present teaching.

As shown in FIG. 1, a sensor in accordance with the present teaching includes a sensor substrate 100 having an upper surface 105 and a lower surface 110. The upper surface is configured to define or support one or more sensor sites—shown here as one sensor site 115 located in a region on the interface between the substrate and what is termed the superstrate region. On excitation of a sample analyte located at that sensor site, light in the form of a luminescence signal 120 will be generated and propagates into the substrate. The luminescence emission is anisotropic. That light propagating at angles greater than the critical angle corresponding to the superstrate/substrate may be considered supercritical angle light and for the typical mediums may be considered as propagating within for example the angular range of ~61.5-75°. It will be appreciated that a luminescence signal may have many different forms depending on the excitation signal. If the signal is a fluorescence signal that resultant luminescence is termed fluorescence and the light propagating at angles greater than the critical angle is called supercritical angle fluorescence (SAF) light. It will be understood and appreciated that if that luminescence light originated from a chemiluminescence or electro-luminescence process, a portion of the light signal will still propagate at angles greater than the critical angle of the superstrate/substrate interface—so called supercritical angles, but it is not appropriate to label it SAF light. It will be further appreciated that the actual angular range will depend on the refractive index of the substrate and superstrate. There may well be supercritical light propagating at angles above 75° as well, but the intensity decreases rapidly for larger angles. For the ease of explanation the following exemplary arrangements will be described with reference to SAF light.

As shown in the cross section of FIG. 1, the lower surface 110 of the substrate 100, which is substantially parallel with the substrate upper surface, is configured to define a recess 125 which is dimensioned to co-operate and interface with a corresponding protrusion 130 that is formed on an upper surface of a corresponding redirection element, in this exemplary arrangement a redirection element that is configured to define a paraboloidal element 131. It will be appreciated that the view of FIG. 1 provides an impression of multiple recesses and protrusions but this is a result of the cross section view, in that a perspective view would show a single ring shaped recession extending about a region defined within the lower surface 110 of the substrate and a corresponding single protrusion provided in a corresponding ring shaped configuration in the upper surface of the redirection element 131. By providing matching structures on the lower surface of the substrate and the upper surface of the paraboloidal element a tight interference fit may be formed by a presentation of the paraboloidal element to the substrate. In this arrangement, the recesses defines an exit face 135, which is substantially parallel with an entry face 140 of the paraboloidal element protrusion. In this way SAF light that exits the substrate will transit a very small gap between each of the two structures prior to entry into the paraboloidal element. It will be understood that at each of the exit from the substrate and corresponding entry to the paraboloidal element that refraction will occur. The refraction however is firstly complimentary in that the light will be deviated a first direction on exiting the substrate and a second opposite direction on re-entry to the paraboloidal element. Furthermore arising from the very small gap between the two structures, the effect of the refraction will be minimal.

Figure 2:
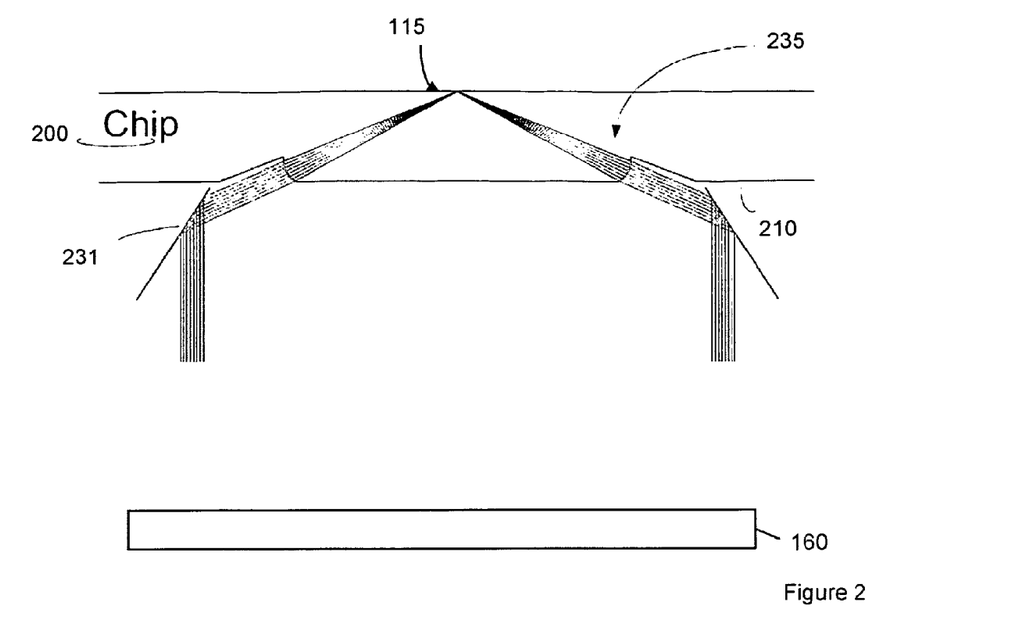
FIG. 2 is a schematic showing another configuration in accordance with the present teaching using an integrated optical element which refocuses the light with the help of a conical mirror.

Outer surfaces 145 of the paraboloidal element are dimensioned to define a paraboloidal surface. The light propagating internally within the paraboloidal element contacts these surfaces and resulting from the relative angles of the surface relative to the propagation path of the light, is totally internally reflected and redirected downwardly in a substantially collimated form. It is then incident substantially orthogonally onto a lower surface 150 of the paraboloidal element such that it exits the paraboloidal element un-deviated and passes 155 towards a detector 160. When viewed from below, the SAF light forms a substantially circular pattern on exiting the paraboloidal element which through judicious location of the detector to the substrate, baffling or a combination of the two, can be preferentially collected by a detector—typically of the type provided by a CMOS or CCD array. It will be appreciated that the detector arrangement 160 is shown as a single block. However this block is intended to include typical elements that would be found in detector assemblies where appropriate. For example, the detector assembly may be considered as including a detector proper preceded by a filter, a lens and an aperture. The filter is normally a narrow band gap interference filter, which takes away unwanted wavelengths from, for example, ambient light and excitation light. These filters are normally designed for normal incidence, hence the need to collect the light in a collimated bundle. The lens then focuses the light onto the detector through an aperture, which helps to remove additional unwanted light, since only light from the sensor site will be focused through the aperture. Therefore while now shown, it will be appreciated that the detector arrangement 160 may include one or more of the following optical elements:

A filter which filters out unwanted wavelengths
  A lens focusing the (usually collimated) light towards the detector
  A pinhole through which through which the light is focused to block out additional unwanted light
  The actual detector By providing an inter-engagement between the co-operable elements of the substrate and the solid paraboloidal element an optical path between the two is established without the use of immersion oil. It will be appreciated that the accurate fabrication of the substrate and cooperating paraboloidal element of FIG. 1 is necessary to provide the necessary inter-engagement sufficient to provide the tight fit and small gap between the two. This can present difficulties in mass production. Furthermore the accurate fabrication of paraboloidal surfaces is not trivial. A second arrangement in accordance with the present teaching is shown in FIG. 2 where the same reference numerals are used for similar components. In this arrangement a substrate 200 with a modified lower surface 210 is again provided. In this arrangement however, the modification of the lower surface is incorporation of a ring lens 235 into the substrate, the ring lens providing a redirection of the propagating SAF light out of the substrate 200. This sensor substrate is configured to be co-operable with complimentary optical elements including for example a conical mirror 231 provided as a separate element to the substrate 200. The light exits the substrate through the ring lens and then is reflected off the conical mirror 231 onto the detector 160. This ring lens is designed to deviate the light to help in collimating it. As shown in the Figure, the deviated rays which are formed into a collimated bundle by the conical mirror. Similarly to FIG. 1, optical contact is not required between the optical elements downstream of the substrate on which the sensor site is provided. In this arrangement of FIG. 2, the 'ring lens' together with the conical mirror and a focusing lens outside the chip will refocus the SAF light without needing a paraboloidal element which as described above may be difficult to mass produce. However in such an arrangement, the emission light forms a large collimated ring of light, requiring a large lens for focusing and more importantly, either a very large emission filter or a smaller filter after the lens.

Figure 3:
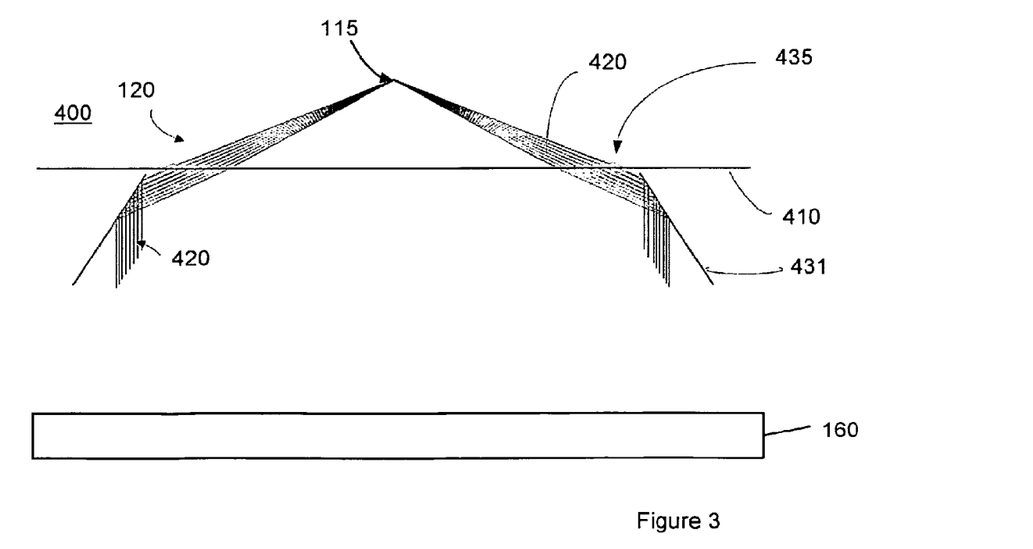
FIG. 3 shows in schematic form the incorporation of a Fresnel structure into a lower surface of a substrate in accordance with present teaching.

FIG. 3 shows a further modification to the lower surface of the substrate 400 where a shallow Fresnel-like structure 435 is formed on the lower surface 410 as an integrated optical element. It will be appreciated that a Fresnel structure comprises a plurality of concentric rings, each of the rings consisting of a thin part of a simple lens. By providing such a perturbation on the lower surface of the substrate, the SAF light 120 that is propagating within the substrate 400, and which would normally be totally internally reflected at the lower surface 410, is transmitted out of the substrate. The Fresnel structure 435 also effects a modification of the propagating beam 120 from a diverging beam to one which is substantially collimated 420. In this way a simple mirror surface or reflector 431 can be used to reflect the collimated beam 420 downwardly towards a detector 160. As the Fresnel rings may be fabricated through a moulding process it is possible to easily integrate these into the substrate at a moulding stage. Furthermore, such rings form a shallow perturbation on the lower surface which will not affect the structural integrity of the substrate, allowing the substrate to be maintained as a relatively thin structure and obviating the possibility of the formation of sink marks on the top surface of the substrate. The Fresnel structure in combination with the complementary reflector enables a refocusing of the light. An advantage of such an arrangement is that it may be used with a detector with a small aperture and thus block any ambient/auto-fluorescent/scattered light etc to reach the detector.

Figure 4:
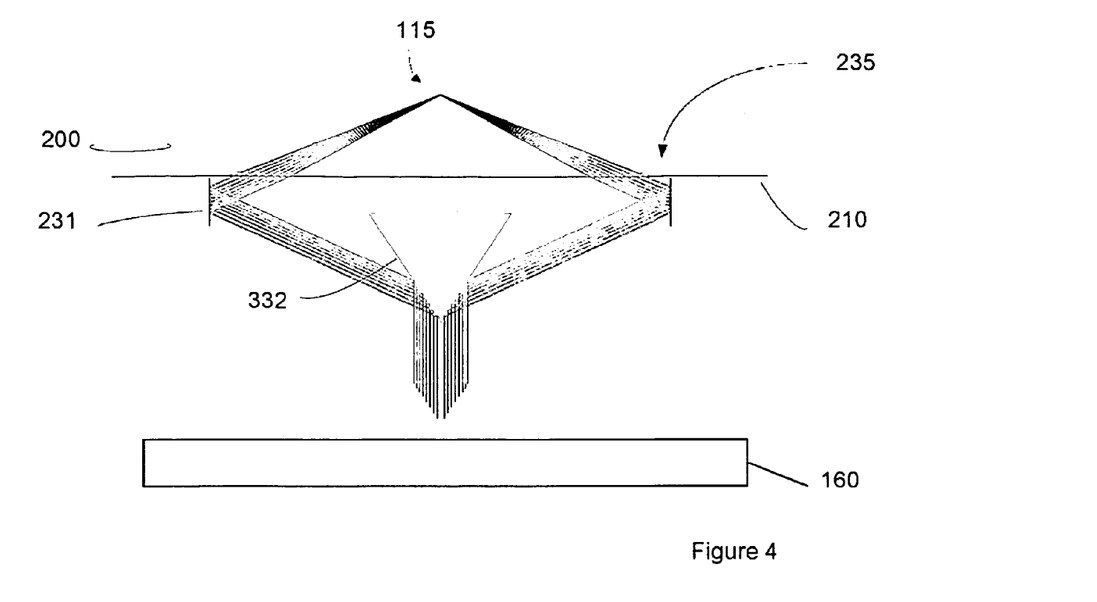
FIG. 4 is a modification to the arrangement of FIG. 3 with a combination of a cylindrical and a conical mirror to provide a smaller light bundle reduces the required size of the optics in the detector system.

FIG. 4 shows a modification to such an arrangement of FIG. 3 which provides a cylindrical 332 mirror in combination with the conical mirror 231. In this way the emitted light forms a much smaller collimated bundle, which can be filtered and refocused with smaller (and cheaper) elements and may also obviate the need for large filters.

Figure 5:
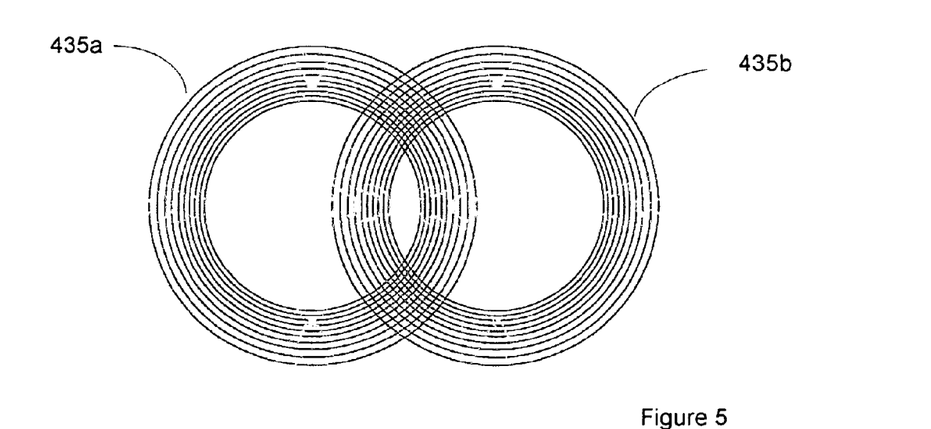
FIG. 5 shows in plan view how two adjacent neighbouring Fresnel structures may be configured to overlap, each of the structures being associated with a specific sensor site thereby allowing for an increase in the density of sensor sites on the upper surface of the substrate.

The use of Fresnel structures such as shown in FIGS. 3 and 4 is highly advantageous in that it allows for a plurality of sensor sites 115 to be provided on the upper surface in close proximity to one another—even close enough such that the SAF light that propagates from each of the immediately adjacent and neighbouring sites can overlap within the substrate. As shown in FIG. 5, which is a plan view of two neighbouring Fresnel structures 435a, 435b, the lower surface of the substrate may be patterned to have each of the two structures overlapping with one another. First and second sensor sites, each being formed at a location on the upper surface of the substrate corresponding with the mid-point of their respective Fresnel structures may therefore be much closer to one another than if the Fresnel structures could not overlap.

Figure 6:
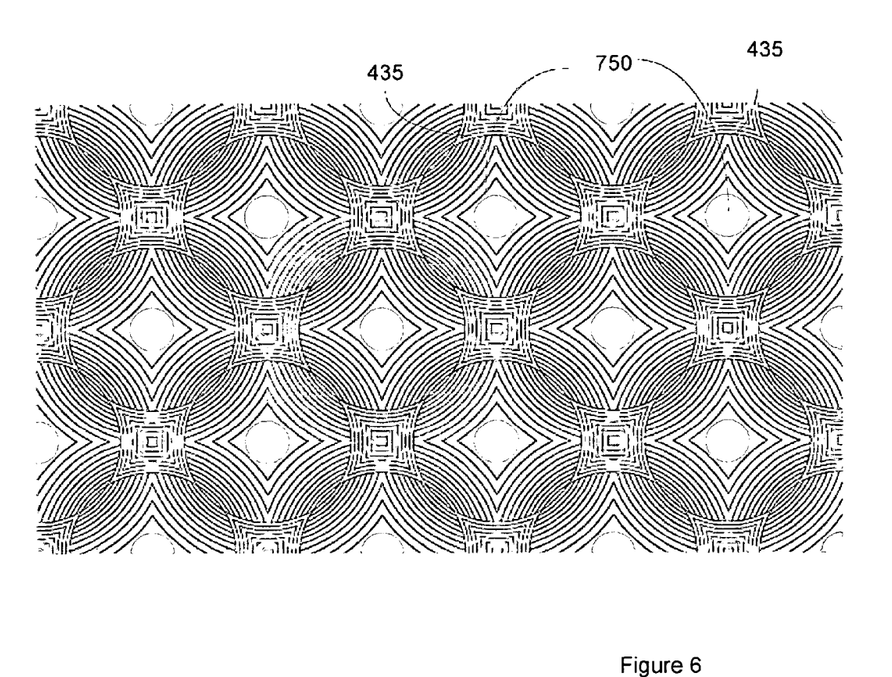
FIG. 6 shows in a graphical form the provision of a plurality of patterned Fresnel structures.
Figure 7:
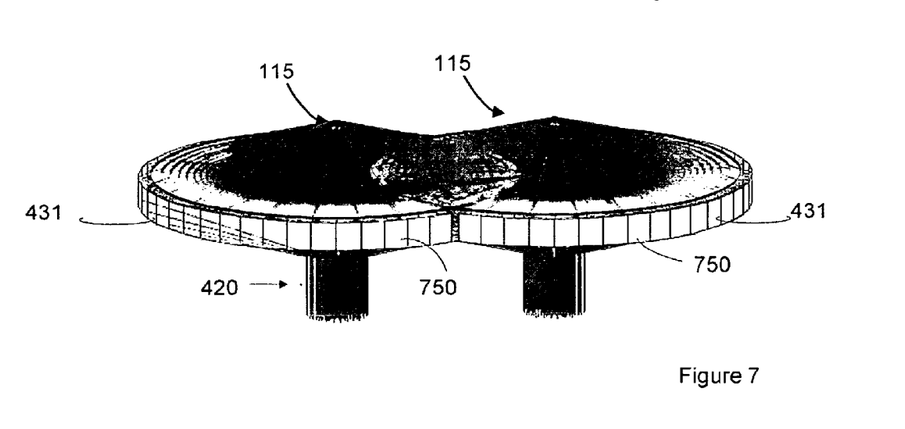
FIG. 7 is a schematic showing in 3-D an exemplary arrangement for two adjacent sensor sites.

FIG. 6 shows a more complicated arrangement derived from this simple example and shown in plan view, where many overlapping structures are provided. As shown in FIG. 7, each of the structures may be provided with a co-operating lens 750, the lenses being arranged coaxially with the centre of their respective Fresnel structure for focusing the excitation light that has been transmitted out of the substrate by the Fresnel structure and reflected by the co-operating optical element.

It will be appreciated that each of the individual rings of the Fresnel structure provide for a refraction of the SAF light out of the substrate. The individual elements of the refractive structure can be mathematically described as follows:

$$\alpha = \varphi_0 - \arctan\left(\frac{\sin\theta}{\frac{n_1}{n_2} - \cos\theta}\right) - \theta$$

Where $\alpha$ is the angle of the element with the horizontal surface of the substrate, $\varphi_0$ the apparent angle of refraction from the horizontal surface of the substrate and $\theta$ the difference in angle between the incident and the refracted light.

Figure 8:
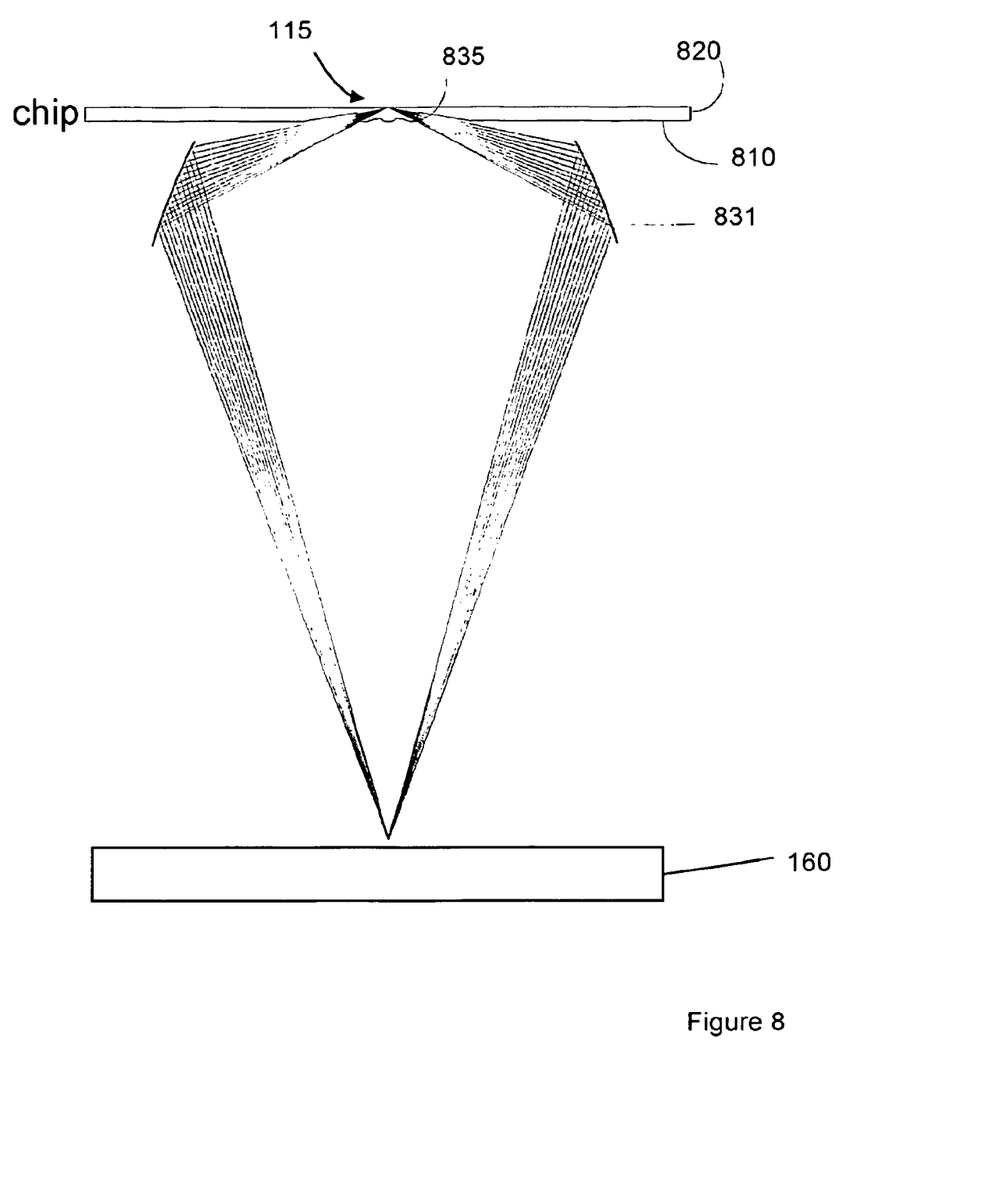
FIG. 8 shows an alternative arrangement where a spherical integrated element allows light to pass un-refracted and an elliptical element is used to provide focussing.
Figure 9:
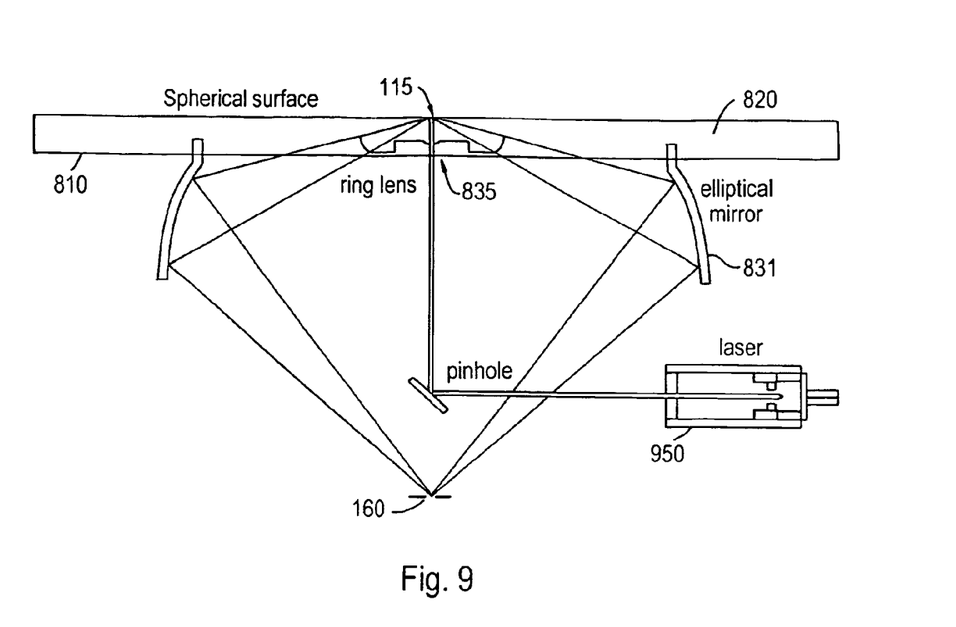
FIG. 9 show a ray tracing diagram for the structure of FIG. 8 illustrating the passage of light through a sensor system incorporating a substrate such as that described in FIG. 8.
Figure 10:
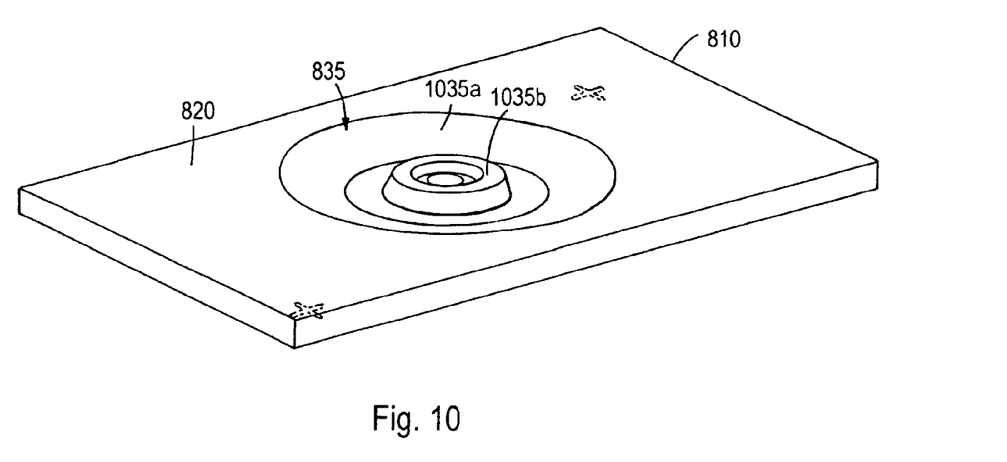
FIG. 10 shows a view from below in perspective of a substrate such as that shown in FIGS. 8 and 9.

FIGS. 8 to 10 shows a further configuration that may be usefully employed within the context of the present teaching to provide for a transmission of otherwise totally internally reflected SAF light out through the lower surface 810 of the substrate 820 within which it is propagating. In this configuration, which is similar to the arrangement of FIG. 2, a simple spherical ring structure 835 is defined in instead of ring lens. Therefore no refraction takes place. The SAF-light is focused by an elliptical hollow mirror 831 onto a detector 160 provided below. It will be understood that using such a configuration that the ring-shaped spherical structure on chip collects SAF light without refraction but there is substantially no collimation of the light The SAF-light transits the structure orthogonally and hits an elliptical hollow mirror 835 which focuses the SAF light. As very few parts are needed, this design is a very simple and cheap way to build up a confocal optical setup for collecting light. In the view of the bottom surface as shown in FIG. 10, it will be seen that the ring structure 835 comprises a plurality of individual surfaces 1035a, 1035b which are defined in the bottom surface 810 and extend inwardly from the bottom of the substrate. These spacings and dimensions of these individual surfaces may be optimised for efficient capture of the SAF light.

While it is not intended to limit the teaching of the present invention to any one excitation principle, FIG. 9 shows how by using a light source 950 (provided in this exemplary arrangement as a laser) provided below the substrate that the sensor site 115 may be excited from below. The light may be collimated or otherwise optimised through the use of pinholes and the like as will be appreciated by those of skill in the art. It will be appreciated that such excitation of a sample from below the substrate may be employed with any one of the other configurations heretofore described.

Figure 11:
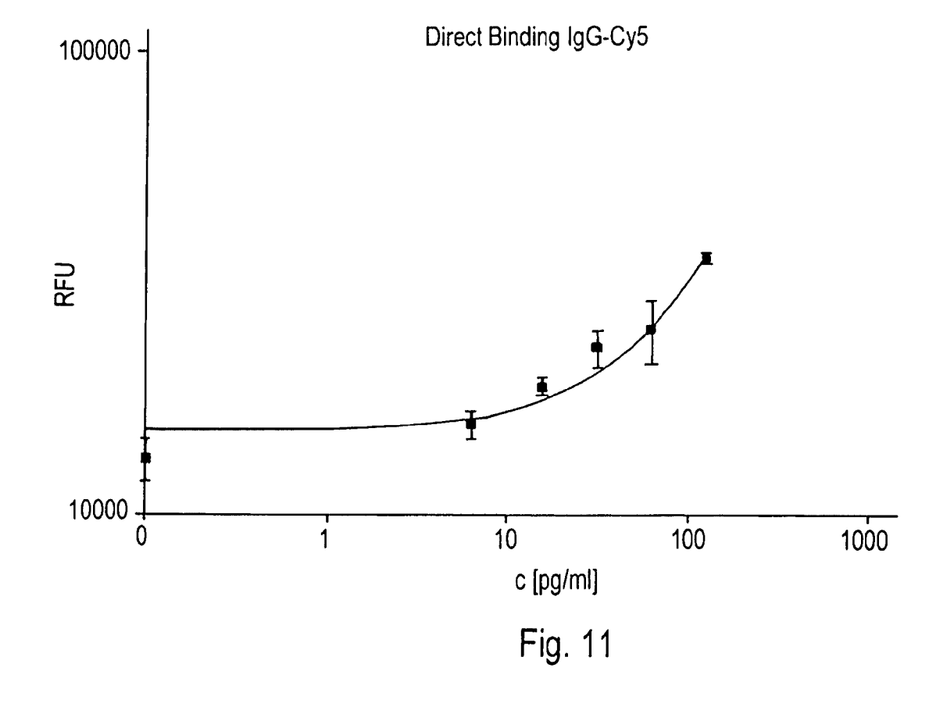
FIG. 11 shows a graph demonstrating light detected from a human-IgG assay bound onto a chip such as that shown in FIG. 9 or 10.

FIG. 11 shows how a ring shaped spherical structure such as that shown in FIGS. 9 and 10 may be used to allow SAF light originating from a human IgG sample bound to an upper surface of the substrate to provide a sample site may then exit the substrate at the relevant angles without refraction. The SAF-light exits the structure orthogonally and hits the elliptical hollow mirror 831 which focuses the SAF light to a detector 160.

It will be appreciated and understood that the configurations described heretofore employ static optics and can be used to preferentially collect and refocus SAF light that would otherwise be retained within the substrate within which it is normally propagating. By providing one or more perturbations on the lower surface of the substrate it is possible to provide relatively shallow substrate structures without affecting the integrity of upper surfaces of the substrate. It is possible to provide an optical path between multiple elements of an optical system without requiring immersion oil or other fluidic optical contacting components between the individual elements. It is also possible to generate such structure to provide a multiplexed arrangement where two or more sensor sites are fabricated on the same substrate and their generated SAF light overlaps in transmission within the substrate. Such arrangements allow for an increase in the density of the sensor sites on the available surface of the substrate. Using the present teaching it will also be appreciated that it is possible to provide a stationary reader in that no moving parts are required to provide the necessary optical path, It will be understood that exemplary arrangements of a substrate which has a lower surface configured to enhances transmission of light propagating within the substrate within a selected range of emission angles out of the substrate has been described. The substrate may be used with a co-operating reflective optical element which provides for redirection of the transmitted light towards a detector. One of the main advantages provided in accordance with the present teaching is that the sensor system facilitates collection of SAF, and by preserving the continuous nature of the substrate's upper surface, allows the benefits of SAF collection to be brought to optical sensor applications that require the patterning of sensor sites. In addition, the simple geometry of each of the exemplary arrangements allows for fabrication at low cost by a number of methods. It will be appreciated that by using a plurality of sensor sites that such a system may be configured for use in multi-analyte applications.

The words comprises/comprising when used in this specification are to specify the presence of stated features, integers, steps or components but does not preclude the presence or addition of one or more other features, integers, steps, components or groups thereof.

The invention claimed is:

1. A sensor comprising:
   a detector;
   a substrate arranged above the detector, the substrate having a first surface and a second surface parallel to the first surface and having a ring lens formed therein, the first surface having at least one sensor site provided thereon, the substrate configured such that on excitation of a sample provided at the sensor site, luminescence originating from the sensor site propagates into the substrate, the ring lens formed in the second surface of the substrate configured to selectively transmit the luminescence propagating within the substrate at angles greater than the critical angle out of the substrate; and
   a separate reflective optical element comprising a conical mirror being circularly symmetric when viewed along an axis passing through the at least one sensor site and which is perpendicular to the first surface and the second surface of the substrate, the conical mirror being co-operatively arranged with the substrate to provide for redirection of the transmitted light towards the detector where the transmitted light is detected, the ring lens and conical mirror being arranged relative to one another such that the light operably exits the substrate through the ring lens and is collimated by the conical mirror prior to detection by the detector,
   and wherein the second surface of the ring lens defines a recess within which a co-operable protrusion of a surface of the reflective optical element is receivable.

2. The sensor of claim 1 wherein the second surface is configured to effect a transmission of the luminescence propagating within the substrates at angles greater than the critical angle out of the substrate through a refraction process.

3. The sensor of claim 1 further comprising a focusing lens provided to focus light reflected by the conical mirror onto the detector.

4. A sensor comprising:
   a detector;
   a substrate arranged above the detector, the substrate having a first surface and a second surface parallel to the first surface and having a ring optical element formed therein, the first surface having at least one sensor site provided thereon, the substrate being configured such that on excitation of a sample provided at the sensor site, luminescence originating from the sensor site propagates into the substrate, the ring optical element formed in the second surface of the substrate being configured to selectively transmit the luminescence propagating within the substrate at angles greater than the critical angle out of the substrate; and
   a reflective optical element co-operatively arranged with the substrate to provide for redirection of the transmitted light towards the detector where it is detected,
   and wherein the reflective optical element defines a paraboloidal element, the ring optical element and the reflective optical element being configured to inter-engage with one another and wherein the second surface of the ring optical element defines a recess within which a co-operable protrusion formed on a surface of the reflective optical element is receivable.

5. The sensor of claim 4 wherein the recess defines an exit face which is substantially parallel with an entry face of the protrusion defined in the reflective optical element.

6. The sensor of claim 5 wherein the reflective optical element is configured such that on receipt of light transmitted out of the ring optical element through the entry face, the light propagates internally within the reflective optical element until it is totally internally reflected against a paraboloidal side wall of the reflective optical element which effects a redirection of the light towards the detector.

7. The sensor of claim 6 wherein the paraboloidal side wall is orientated relative to the propagation path of the light such that the light, on reflection by the paraboloidal wall is totally internally reflected and redirected downwardly in a substantially collimated form.

8. The sensor of claim 1 wherein the first surface is substantially continuously planar.

9. The sensor of claim 1 wherein the second surface comprises one or more perturbations defined therein, the perturbations providing for a selective transmission of the luminescence propagating within the substrates at angles greater than the supercritical angle out of the substrate.

10. The sensor of claim 1 wherein the luminescence propagating within the substrates at angles greater than the supercritical angle is a fluorescence signal.

11. The sensor of claim 1 wherein the luminescence propagating within the substrates at angles greater than the supercritical angle is a chemi-luminescence signal or an electro-luminescence signal.

12. The sensor of claim 1 configured for use with a detector provided below the substrate.

13. The sensor of claim 12 comprising an excitation source configured for use with an excitation source provided below the substrate.

14. The sensor of claim 1 comprising a plurality of sensor sites, each of the sensor sites providing a bio-recognition site.

15. A sensor comprising:
   a first optical element comprising a substrate having a first surface and a second surface, the first surface having at least one sensor site provided thereon, the substrate configured such that on excitation of a sample provided at the sensor site, luminescence originating from the sensor site propagates into the substrate, the second surface of the substrate comprising a ring lens configured to selectively transmit the luminescence propagating within the substrate at angles greater than the critical angle out of the substrate where it is detected by a detector provided below the substrate; and a second optical element comprising a conical mirror, the second optical element being arranged relative to the first optical element to effect a reflection and collimation of light exiting the substrate towards the detector, and wherein the second surface of the ring lens defines a recess within which a co-operable protrusion formed on a surface of the second optical element is receivable.

16. The sensor of claim 15 further comprising a focusing lens provided to focus light reflected by the second optical element onto the detector.

17. A sensor comprising:

a first optical element comprising a substrate having a first surface and a second surface, the first surface having at least one sensor site provided thereon, the substrate being configured such that on excitation of a sample provided at the sensor site, luminescence originating from the sensor site propagates into the substrate, the second surface of the substrate being configured to selectively transmit the luminescence propagating within the substrate at angles greater than the critical angle out of the substrate where it is detected by a detector provided below the substrate; and a second optical element defining a paraboloidal element, the first and second optical elements being configured to inter-engage with one another, the second optical element being arranged relative to the first optical element to effect a reflection and collimation of light exiting the substrate towards the detector and wherein the second surface of the first optical element defines a recess within which a co-operable protrusion formed on a surface of the second optical element is receivable.

18. The sensor of claim 17 wherein the recess defines an exit face which is substantially parallel with an entry face of the protrusion defined in the second optical element.

19. The sensor of claim 18 wherein the second optical element is configured such that on receipt of light transmitted out of the first optical element through the entry face, the light propagates internally within the second optical element until it is totally internally reflected against a paraboloidal side wall of the second optical element which effects a redirection of the light towards the detector.

20. The sensor of claim 19 wherein the paraboloidal side wall is orientated relative to the propagation path of the light such that the light, on reflection by the paraboloidal wall is totally internally reflected and redirected downwardly in a substantially collimated form.

\* \* \* \* \*

UNITED STATES PATENT AND TRADEMARK OFFICE
CERTIFICATE OF CORRECTION

PATENT NO. : 9,291,558 B2
APPLICATION NO. : 13/697278
DATED : March 22, 2016
INVENTOR(S) : Jim Writser Peter Bakker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 342 days.

Signed and Sealed this
Twenty-sixth Day of July, 2016

Michelle K. Lee
*Director of the United States Patent and Trademark Office*